United States Patent [19]

Caswell et al.

[11] Patent Number: 5,857,977
[45] Date of Patent: Jan. 12, 1999

[54] METHOD AND APPARATUS FOR SEPARATION OF VENTRICULAR TACHYCARDIA FROM VENTRICULAR FIBRILLATION FOR IMPLANTABLE CARDIOVERTER DEFIBRILLATORS

[75] Inventors: Stephanie A. Caswell; Janice M. Jenkins; Lorenzo A. DiCarlo, all of Ann Arbor, Mich.

[73] Assignee: The Regents of the University of Michigan, Ann Arbor, Mich.

[21] Appl. No.: 694,189

[22] Filed: Aug. 8, 1996

[51] Int. Cl.$^6$ .................................................... A61B 5/046
[52] U.S. Cl. .............................................................. 600/518
[58] Field of Search .................................... 128/705, 702, 128/706, 696; 607/4, 5; 600/518, 515, 519, 509

[56] References Cited

U.S. PATENT DOCUMENTS

| | | | |
|---|---|---|---|
| 4,667,682 | 5/1987 | Ihlenfeld, III | 128/705 |
| 4,991,583 | 2/1991 | Silvian | 607/13 |
| 5,107,850 | 4/1992 | Olive | 607/4 |
| 5,193,535 | 3/1993 | Bardy et al. . | |
| 5,193,550 | 3/1993 | Duffin | 128/705 |
| 5,513,645 | 5/1996 | Jacobson et al. | 128/705 |
| 5,558,098 | 9/1996 | Fain | 128/706 |

OTHER PUBLICATIONS

Anthony D. Mercando et al., "Measurement of Differences in Timing and Sequence Between Two Ventricular Electrodes as a Means of Tachycardia Differentiation", PACE, vol. 9, Nov.–Dec. 1986, Part II, pp. 1069–1078.

Chih–Ming James Chiang et al., "Digital Signal Processing Chip Implementation for Detection and Analysis of Intracardiac Electrograms", PACE, vol. 17, Aug. 1994, pp. 1373–1379.

Gregory K. Jones et al., "Considerations for ventricular fibrillation detection by implantable cardioverter defibrillators", American Heart Journal, vol. 127, No. 4, Part 2, 1994, pp. 1107–1110.

Gust H. Bardy, "Ensuring Automatic Detection of Ventricular Fibrillation", American Heart Association, Division of Cardiology, Department of Medicine, University of Washington, Editorial, pp. 1634–1635.

Gust H. Bardy et al., "Clinical Experience With a Tired–Therapy, Multiprogrammable Antiarrhythmia Device", Circulation, vol. 85, No. 5, May 1992, pp. 1689–1698.

Gust H. Bardy et al., "Implantable Transvenous Cardioverter–Defibrillators", Circulation, vol. 87, No. 4, Apr. 1993, pp. 1152–1168.

(List continued on next page.)

*Primary Examiner*—William E. Kamm
*Assistant Examiner*—Kennedy J. Schaetzle
*Attorney, Agent, or Firm*—Harness, Dickey & Pierce, P.L.C.

[57] ABSTRACT

A method and appartus for differentiating between ventricular tachycardia and ventricular fibrillation includes a pair of electrodes located on a single catheter which, in conjunction with an implantable cardioverter device, utilize two channel ventricular algorithms for ventricular tachycardia and ventricular fibrillation separation. Two closely spaced unipolar electrograms demonstrate similar morphology and consistency during rhythms with broad coherent activation (such as sinus rhythm and ventricular tachycardia). Conversely, for incoherent rhythms (ventricular fibrillation and polymorphic ventricular tachycardia), activation between the electrodes proved to be dissimilar and inconsistent. The cross-correlation of the two depolarizations measures similarity between electrogram morphology, and interquartile range measures consistency in a passage. The method and apparatus of the present invention is able to address the limitation of existing algorithms and provide accurate separation of ventricular fibrillation from other rhythms.

20 Claims, 4 Drawing Sheets

OTHER PUBLICATIONS

H.–J. Geywitz et al., "Programming VT and VF Detection Criteria", Practical Aspects of Staged Therapy Defibrillators, Chapter 21, 1992, pp. 113–118.

Janice M. Jenkins et al., "Is Waveform Analysis a Viable Consideration for Implantable Devices Given Its Computational Demand?", IEEE, 1993, pp. 839–842.

Janice M. Jenkins et al., "Detection Algorithms in Implantable Cardioverter Defibrillators", Proceedings of the IEEE, vol. 84, No. 3, Mar. 1996, pp. 428–445.

Kristina M. Ropella et al., "Differentiation of Ventricular Tachyarrhythmias", Circulation, vol. 82, No. 6, Dec. 1990, pp. 2035–2043.

Kristina M. Ropella et al., "The Coherence Spectrum: A Quantitative Discriminator of Fibrillatory and Nonfibrillatory Cardiac Rhythms", Circulation, vol. 80, No. 1, Jul. 1989, pp. 112–119.

Lauri Toivonen et al., "The Performance of the Probability Density Function in Differentiating Supraventricular from Ventricular Rhythms", PACE, vol. 15, May 1992, pp. 726–730.

Lorenzo A. DiCarlo et al., "Differentiation of Ventricular Tachycardia from Ventricular Fibrillation Using Intraventricular Electrogram Morphology", The American Journal of Cardiology, vol. 70, Sep. 15, 1992, pp. 820–822.

Lorenzo DiCarlo et al., "Tachycardia Detection by Antitachycardia Devices: Present Limitations and Future Strategies", Journal of Interventional Cardiology, vol. 7, No. 5, 1994, pp. 459–472.

N. Thakor et al., "Ventricular Tachycardia and Fibrillation Detection by a Sequential Hypothesis Testing Algorithm", IEEE Transactions on Biomedical Engineering, vol. 37, No. 9, Sep. 1990, pp. 837–843.

R.A. DuFault et al., "Dual Lead Fibrillation Detection for Implantable Defibrillators via LMS Algorithm", IEEE, 1987, pp. 163–166.

Robert D. Throne et al., "Scatter Diagram Analysis: A New Technique for Discriminating Ventricular Tachyarrhythmias", PACE, vol. 17, Jul. 1994, pp. 1267–1275.

S. Chen et al., "Ventricular Fibrillation Detection by a Regression Test on the Autocorrelation Function", Medical & Biological Engineering & Computing, May 1987, pp. 241–249.

T. Rolf Turner et al., "Statistical Discriminant Analysis of Arrhythmias using Intracardial Electrograms", IEEE Transactions on Biomedical Engineering, vol. 40, No. 9, Sep. 1993, pp. 985–989.

V.E. Paul et al., "Variability of the Intracardiac Electrogram: Effect on Specificity of Tachycardia Detection", PACE, vol. 13, Dec. 1990, Part II, pp. 1925–1929.

METHOD AND APPARATUS FOR SEPARATION OF VENTRICULAR TACHYCARDIA FROM VENTRICULAR FIBRILLATION FOR IMPLANTABLE CARDIOVERTER DEFIBRILLATORS

The present invention was supported by grants from the National Science Foundation (grant no. GER-9023514) and the Whitaker Foundation.

FIELD OF THE INVENTION

The present invention relates generally to the differentiation of ventricular tachycardia from ventricular fibrillation in an implantable cardioverter defibrillator. More particularly, the present invention relates to a method and apparatus for differentiating ventricular tachycardia from ventricular fibrillation using the concordance between a pair of unipolar signals integrated with an implantable cardioverter defibrillator.

BACKGROUND OF THE INVENTION

The heart may be viewed as a spontaneous current generator whose pumping action is effected by spontaneous generation of an electrical impulse (known as an action potential), conduction of the electrical impulse throughout the heart, and subsequent contraction of the heart muscle (myocardium) in response to the impulse. It is, therefore, electrical activity which initiates and controls muscular contraction of the heart.

Chemicals in the form of ions (such as sodium, potassium and chloride) reside in the extracellular and intracellular fluid of a muscle cell. The concentration gradients of these ions combined with cell membrane features make for a special ion arrangement at the inner and outer wall of the cell membrane. At rest, this special membrane arrangement produces a negative transmembrane potential. If the cell membrane is stimulated by an electrical impulse of adequate magnitude and proper polarity, a process known as an "action potential" will ensue. During an action potential a cell depolarizes (transmembrane potential becomes less negative) and then repolarizes (transmembrane potential returns to resting value). The impulse of adequate magnitude naturally comes from a neighboring cell undergoing an action potential. Thus, impulses are propagated through the heart via a cell-to-cell mechanism.

The heart's electrical impulse originates in the sino-atrial node and is transmitted (cell-to-cell) to all portions of the atria, resulting in the contraction of the atrial chambers. The electrical impulse continues in its path to reach a cluster of conduction fibrils known as the atrioventricular node, or the A-V node. By delaying conduction for approximately one-tenth of a second, the A-V node acts as a buffer for impulses from the atria to the ventricles. This allows for proper flow of blood from the atria to the ventricles.

Following this delay, the A-V node transmits an impulse that reaches another cluster of fibers known as the bundle of His which comprises left and right bundle branches of the His-Purkinjie system. The bundle branches terminate with the Purkinjie fibers which are themselves attached directly to the myocardial cells.

A coordinated wave of electrical impulses effects contraction of many myocardial cells simultaneously, thus causing the heart's pumping action. The action begins in the sino-atrial node from which impulses are provided spontaneously and periodically. The impulses travel to the surrounding cardiac tissue and propagate as a wave of depolarization. As noted above, contracting of the cardiac muscle of the atria follows after the depolarization. Subsequent ventricular conduction is initiated via the A-V node and the His-Purkinjie system.

Normal electrical function provides for continued proper functioning of the heart. However, aberrations in electrical origination or transmission produce concomitant malfunctions of the systemic delivery of blood to the body. The majority of cases of cardiac malfunction may be traced to a failure in the electrical conduction system of the heart. The result of such an electrical failure or change from the normal electrical activity and sequence of cardiac activity is an arrhythmia. Arrhythmias may be atrial, atrioventricular, or ventricular. Two of the most deadly forms of arrhythmia are ventricular tachycardia and ventricular fibrillation. Both of these events are generally defined as sustained ventricular arrhythmias.

In ventricular tachycardia, the sequence of ventricular extrasystoles occur at a rate of between 110 to 240 cycles per minute. This type of arrhythmia is characterized by atrioventricular dissociation, an abnormally wide QRS complex (surface lead electrodes), and a far more rapid rate than usual.

Ventricular fibrillation sometimes preceded by a sustained ventricular tachycardia reaches a frequency in excess of 330 cycles per minute. Ventricular fibrillation is not a cessation of electrical activity, but is actually characterized by incoherent electrical activity throughout the ventricle. This loss of succinct conduction of electrical activity prevents any reasonable contraction of the heart and therefore prevents pumping of blood to the body. If therapy is not given, beyond five minutes inadequate blood will result in loss of brain function and, beyond ten minutes, death will occur.

Several methods are known to treat arrhythmia. Drugs are occasionally prescribed, and, while having significant side effects, are often justified because of the severity of the arrhythmia. Drugs, called calcium antagonists, mediate the heart's conduction by halting electrical conduction through the blocking of the calcium channels of myocardial cells. Nitrates may be used as treatment in cases of acute myocardial infarction or congestive heart failure.

Another therapeutic technique is referred to as radio frequency ablation which is directed to neutralizing accessory electrically-conductive pathways of the heart which cause the heart to fail in properly conducting electrical impulses due to some small area of the heart which is skewing the direction of depolarization. In this technique, a catheter is introduced into the heart and a delivery of high frequency radio waves is used to burn away the faulty area of the heart. Following successful radio frequency ablation therapy, normal conduction of the heart will return and the particular arrhythmia associated with the damaged tissue will be eliminated.

One of the most common approaches for termination of an arrhythmia, instead of prevention, is electrical therapy in which electrodes are fitted to either the body or the heart for selectively delivering an electrical current or shock to alter the rhythm of the heart. Implantable cardioverter defibrillators, or "ICDs", are devices which are implanted and stimulate the heart directly using function generators with specific waveforms to respond to and treat arrhythmias on an "as-needed" basis.

Implantable cardioverter defibrillators have achieved overwhelming success in salvaging thousands of lives by providing immediate electrical therapy for the treatment of potentially lethal arrhythmias, i.e., ventricular tachycardia and ventricular fibrillation. These rhythms are believed responsible for over 80% of cases of sudden cardiac death, which claims 400,000 victims per year. The number of implants of ICDs is exceptional (over 75,000 implants to date), despite its relative infancy in the medical field.

Because of the difference in rates of ventricular extrasystoles between ventricular tachycardia and ventricular fibrillation, a lower amount of defibrillating energy is required for the former than for the latter. An implantable cardioverter defibrillator capable of correctly distinguishing between the two so as to deliver only as much power as the circumstance warrants would produce greater power savings, a situation which is important to extending the life of the unit.

There are known implantable cardioverter defibrillators which supply immediate defibrillation for ventricular fibrillation and lower-energy therapies of antitachycardia pacing and cardioversion for ventricular tachycardias, the object being largely for the conservation of battery power, but also for greater patient comfort. In general, these devices use heart rate to distinguish ventricular tachycardia from ventricular fibrillation.

More particularly, to distinguish between ventricular tachycardia and ventricular fibrillation, commercially available ICDs increment a counter associated with a detection zone based on the most recent cycle length. Measuring cycle length is dependent on an accurate sensing of each depolarization by a trigger. However, electrogram dropout (missed triggers) during ventricular fibrillation produces low estimates of the ventricular fibrillation rate which severely overlap ventricular tachycardia rates making ventricular tachycardia and ventricular fibrillation indistinguishable. (This is particularly problematic in the event of tachyarrhythmias in the range of 200 ms to 350 ms since there is a significant overlap in cycle lengths. [See, for example, Caswell et al., Ventricular Tachycardia Discrimination By Antitachycardia Devices, PACE 1996 (unpublished)].) Such electrogram dropouts are common in ventricular fibrillation because of rapidly changing peak amplitudes.

The implantable cardioverter defibrillators commercially available today use rate thresholds and counters to distinguish ventricular tachycardia and ventricular fibrillation. These methods have had limited success for distinctions between ventricular tachycardia and ventricular fibrillation. Other algorithms have been developed in the research setting with some success.

Compensation for ventricular fibrillation sensing limitations, in order to ensure detection of ventricular fibrillation, is typically achieved by lengthening the fibrillation detection interval (FDI), the rate threshold between ventricular tachycardia and ventricular fibrillation. The overriding necessity of fail-safe ventricular fibrillation detection bypasses the use of lower energy therapies tailored for ventricular tachycardia since overly-liberal FDI values invoke defibrillation for many episodes of ventricular tachycardia. Accordingly, due to the necessity of not missing ventricular fibrillation, physicians program devices to deliver defibrillation to these cases, limiting the usefulness of lower energy therapies which save precious battery energy and decrease patient anxiety.

Little information is available concerning discrimination of ventricular tachycardia from ventricular fibrillation for appropriate therapeutic choice of treatment. Some studies claim defibrillation was delivered to true ventricular fibrillation in only 10–21% of shock episodes. (See, for example, Bardy et al., Implantable Transvenous Cardioverter-Defibrillators, Circulation 1993, 87:1152–1168, and Bardy et al., Clinical Experience With A Tiered-Therapy Multiprogrammable Antiarrhythmia Device, Circulation 1992, 85:1689–1698.) Another study used simulators of the three FDA-approved ICDs to test a variety of ventricular tachycardias and ventricular fibrillations (Caswell et al., Ventricular Tachycardia Discrimination By Antitachycardia Devices, PACE 1996 [unpublished]). At nominal parameters, ventricular tachycardia was misdiagnosed as ventricular fibrillation, of greater than 65% of the cases. The PSC invention has been demonstrated to be successful in separating ventricular fibrillation from ventricular tachycardia and sinus rhythm and gives a dramatic improvement over ICD rate methods in current use. Comparatively, one test showed ICDs has specificity of 10% versus 100% specificity for PSC.

In addition to rate, two morphological algorithms for ventricular fibrillation detection were implemented in earlier ICDS, probability density function (PDF) and temporal electrogram analysis (TEA). PDF, the original AICD™ detection scheme, used the derivative to define departure from baseline (Mirowski et al., The Automatic Implantable Defibrillator, Am. Heart J. 1980, 100: 1089–1092). TEA, incorporated in some second-generation devices, identified a change in electrogram morphology by the order which depolarizations crossed predetermined thresholds (Paul et al., Temporal Electrogram Analysis: Algorithm Development, PACE 1990, 13: 1943–1947). Experience with PDF and TEA in first- and second-generation devices was disappointing due to its lack of specificity. As a result, by 1992, less than 15% of ICDs utilized either algorithm for tachycardia discrimination (DiCarlo et al., Tachycardia Detection By Antitachycardia Devices: Present Limitations And Future Strategies, Journal of Interventional Cardiology, 1994, 7: 459–472).

A number of studies have begun to address the problem of separating ventricular tachycardia and ventricular fibrillation. In several studies (see, for example, DiCarlo et al., Differentiation Of Ventricular Tachycardia From Ventricular Fibrillation Using Intraventricular Electrogram Morphology, Am. J. Cardiol., 1992, 70: 820–822 and Jenkins et al., Is Waveform Analysis A Viable Consideration For Implantable Devices Given Its Computational Demand?, Computer in Cardiology, 1993, Los Alamitos: IEEE Computer Society Press, 1993: 839–842) the standard deviation of template-based (TB) algorithms (correlation waveform analysis (CWA), bin area method (BAM), difference of area (DOA), derivative area method (DAM)) was used as a discriminant function and achieved varying degrees of success. Sensitivity ranged from 83% to 100% and specificity from 56% to 100%. Other algorithms utilized statistical methods and are discussed in Thakor et al., Ventricular Tachycardia And Fibrillation Detection By A Sequential Hypothesis Testing Algorithm, IEEE Trans. Biomed Eng., 1990, 37:837–843 and Turner et al., Statistical Discriminant Analysis of Arrhythmias Using Intracardiac Electrograms, IEEE Transactions On Biomedical Engineering 1993, 40:985–989. However, neither study segregated the data into training and test sets thus results are inconclusive.

As described by Chen et al. in Ventricular Fibrillation Detection By A Regression Test On The Autocorrelation Function (Medical and Biological Engineering and Computing, 1987, 25: 241–149), autocorrelation function (ACF) was examined using linearity of the peak values where more linearity indicated monomorphic waveforms and achieved 100% sensitivity and specificity.

Two algorithms (discussed and disclosed in Throne et al., Scatter Diagram Analysis: A New Technique For Discriminating Tachyarrhythmias, PACE 1994, 17:1267–1275 and Ropella et al., Differentiation Of Ventricular Tachyarrhythmias, Circulation 1990, 82:2035–2043) using two distinct signals from the ventricle achieved significant success in discriminating ventricular fibrillation from other rhythms. As described in Throne et al., (supra), corresponding pairs of the two channels were plotted on a scatter diagram (SD). It was found that monomorphic ventricular tachycardias trace nearly the same path and occupy a smaller percentage of SD than non-regular rhythms such as polymorphic ventricular tachycardia (PMVT) or ventricular fibrillation. The development of a two channel algorithm using two separate catheters based on the magnitude squared coherence (MSC) which measures the basic organization of the rhythm in the frequency domain was described by Ropella et al. in Differentiation Of Ventricular Tachyarrhythmias (Circulation 1990, 82: 2035–2043). Lastly, U.S. Pat. No. 5,193,535, issued Mar. 16, 1993, to Bardy et al. for METHOD AND APPARATUS FOR DISCRIMINATION OF VENTRICULAR TACHYCARDIA FROM VENTRICULAR FIBRILLATION AND FOR TREATMENT THEREOF describes an algorithm which uses variability of the timing difference (TIM) between two ventricular signals. The method and apparatus of this reference teaches the quantification of the directional changes in the depolarization of the ventricle.

Each of these teachings suffers from at least one disadvantage. Specifically, the described algorithms may be potentially confounded by atrial fibrillation with ventricular response (AF/FVR) due to its variable rate (ACF), and ventricular premature depolarizations (VPDs) due to variable morphology (ACF, TB, TIM, SD). Other possible limitations of these algorithms include computational complexity, the necessity of a sinus rhythm template which is representative of all time and the introduction of multiple electrode catheters.

Accordingly, the present challenge is to optimize differentiation of ventricular tachycardia from ventricular fibrillation in order to direct appropriate therapy to minimize power consumption of an implantable battery-operated device.

SUMMARY OF THE INVENTION

The present invention responds to these needs by providing an implantable cardioverter device which provides improved discrimination between ventricular tachycardia and ventricular fibrillation.

It is accordingly an object of the present invention to provide a method and apparatus capable of efficiently and correctly distinguishing between ventricular tachycardia and ventricular fibrillation.

A further object of the present invention is to provide such a method and apparatus which is capable of correctly and accurately distinguishing between these two episodes using an arrangement which comprises a minimum number of components with a minimum amount of complexity.

Still another object of the present invention is to provide such a method and apparatus which results in a minimum of energy consumption from the battery of an implantable cardioverter device.

An additional object of the present invention is to provide such a method and apparatus which quantifies the nature of ventricular fibrillation—incoherence—in order to achieve a diagnosis.

A further object of the present invention is to provide such a method and apparatus which allows consideration of lower energy therapies for ventricular tachycardia to provide significant energy savings for the battery powered device and improved patient comfort.

The present invention achieves these and other objects by providing a method and an apparatus which is capable of reliably and efficiently differentiating between ventricular fibrillation and ventricular tachycardia. Specifically, the present invention, entitled "pair signal concordance," utilizes two channel ventricular algorithms for ventricular tachycardia and ventricular fibrillation separation. The paired signal concordance algorithm uses two electrodes located on the same catheter to eliminate the need for multiple leads. According to the present invention, two closely spaced unipolar electrograms demonstrate similar morphology and consistency during rhythms with broad coherent activation (such as sinus rhythm and ventricular tachycardia). Conversely, for incoherent rhythms (ventricular fibrillation and polymorphic ventricular tachycardia), activation between the electrodes proved to be dissimilar and inconsistent. The cross-correlation of the two depolarizations measures similarity between electrogram morphology, and interquartile range measures consistency in a passage. The method and apparatus of the present invention is able to address the limitation of existing algorithms and provide accurate separation of ventricular fibrillation from other rhythms.

This invention offers a considerable improvement over current methods of analysis by employing the additional criterion to rate for reliable separation of ventricular tachycardia and ventricular fibrillation. Particularly, the disclosed concordance measurement quantifies the coherence between two electrode configurations from the same catheter, where incoherence between signals indicates ventricular fibrillation or polymorphic ventricular tachycardia. This method would not necessarily replace typical rate methods, but should be used as a supplement to determine the precise arrhythmia allowing exact therapeutic requirements to be selected. Specifically, with proper distinction of ventricular tachycardia, defibrillation could be deferred for consideration of lower energy therapies, providing significant energy savings.

In comparison with known methods of identifying arrhythmias, three algorithms utilize two electrode configurations to separate ventricular tachycardia from ventricular fibrillation (SD, MSC, TIM). Two algorithms use an electrode configuration which only requires one catheter (SD, TIM). However, none of the signal configurations use two unipolar configurations. CWA also uses correlation as a measure of similarity. However, the concordance algorithm uses the second signal instead of a constant sinus rhythm template. Lastly, no algorithms use IQR as the measure of variance. In other words, each item is not strictly unique, but the combined use in the paired signal concordance algorithm produces an excellent method for separating ventricular tachycardia from ventricular fibrillation, a necessary function for the commercial ICD to provide optimal use of energy.

BRIEF DESCRIPTION OF THE DRAWINGS

The present invention will be more fully understood by reference to the following detailed description of the preferred embodiments of the present invention when read in conjunction with the accompanying drawings, in which like reference characters refer to like parts throughout the views, and in which.

DETAILED DESCRIPTION OF THE PREFERRED EMBODIMENT

The drawings disclose the preferred embodiment of the present invention. While the configurations according to the illustrated embodiment are preferred, it is envisioned that alternate configurations of the present invention may be adopted without deviating from the invention as portrayed. The preferred embodiment is discussed hereafter.

In general, this invention provides an algorithm for properly distinguishing ventricular tachycardia from ventricular fibrillation for use in the implantable cardioverter defibrillator (ICD). Proper distinction would allow delivery of the most cost effective therapy, i.e., providing the therapy which utilizes the least amount of energy, but which is still likely to terminate the rhythm. Lower energy therapies of antitachycardia pacing and cardioversion could be attempted for ventricular tachycardia while defibrillation could be reserved for ventricular fibrillation and as a backup for failure to convert ventricular tachycardia. Rate, the current method of arrhythmia detection, has difficulty in separating ventricular tachycardia and ventricular fibrillation due to the likelihood of electrogram dropout during ventricular fibrillation. This electrogram dropout, resulting from trigger failure in low amplitude ventricular fibrillation signals, causes a lower rate to be sensed than the rate actually present. This mistaken lower rate seriously overlaps ventricular tachycardia rates for which therapeutic pacing or low energy cardioversion may be more suitable. To compensate for failed detection, highly conservative detection zones are programmed by physicians in order not to miss a serious event.

This invention improves upon ambivalent detection with a new paired signal concordance algorithm (PSC). In this algorithm, two separate unipolar signals are derived from two members of a bipolar electrode pair (1 cm spacing) on a single catheter positioned in the right ventricular apex with the can of the ICD being the reference electrode. Bipolar electrode catheters as well as an active can as reference is standard in current technology.

The overall scheme for detection uses an existing rate algorithm as a first pass to determine if a fast rhythm has been achieved. The range in which rate is not a sufficient measure to separate ventricular tachycardia and ventricular fibrillation invokes PSC for proper detection. Once the rate threshold has been met the algorithm digitizes and stores the two signals, derived from the catheter. The minimum sampling rate is utilized in order to maintain proper distinction between ventricular tachycardia and ventricular fibrillation. Signals are stored until a selected number of cycles has been met. This ensures the calculation of the ventricular tachycardia/ventricular fibrillation measure only when necessary. PSC is calculated for the number of beats stored (with the maximum storage allowable being the most recent 24 cycles). The paired signal concordance algorithm quantifies the variability of the similarity between signals recorded 1 cm (or more) apart.

Similarity between electrode morphology is measured by a normalized cross-correlation:

$$\rho(m) = \frac{1}{N-m} \frac{\sum_{n=1}^{n=N} (d(n-m) - \bar{d})(p(n-m) - \bar{p})}{\sqrt{\sum_{n=1}^{n=N} (d(n-m) - \bar{d})^2 \sum_{i=1}^{i=N} (p(n-m) - \bar{p})^2}};$$

$m = -M, \ldots, -1, 0, 1, \ldots, M,$ where:

$\rho(m)$ = the cross correlations values $d(n-m)$ = points of the distal unipolar electrogram $p(n-m)$ = points of the proximal $\bar{d}$ = average of the distal $\bar{p}$ = average of the proximal $N$ = number of points in the window $M$ = number of shifts The cross-correlation is computed for a window (N) centered over the trigger point of the distal lead and then performed for M shifts in each direction to ensure proper alignment and the peak value of the cross-correlation (PCC) is selected. Ventricular fibrillation is separated from ventricular tachycardia/sinus rhythm by the interquartile range (IQR), used as a measure of variability. The IQR is defined as the PCC value at the 75th percentile minus the 25th percentile of the passage. A threshold is set for the IQR which separates ventricular tachycardia and ventricular fibrillation. Early tests indicate the threshold should be approximately 0.5.

Figure 1:
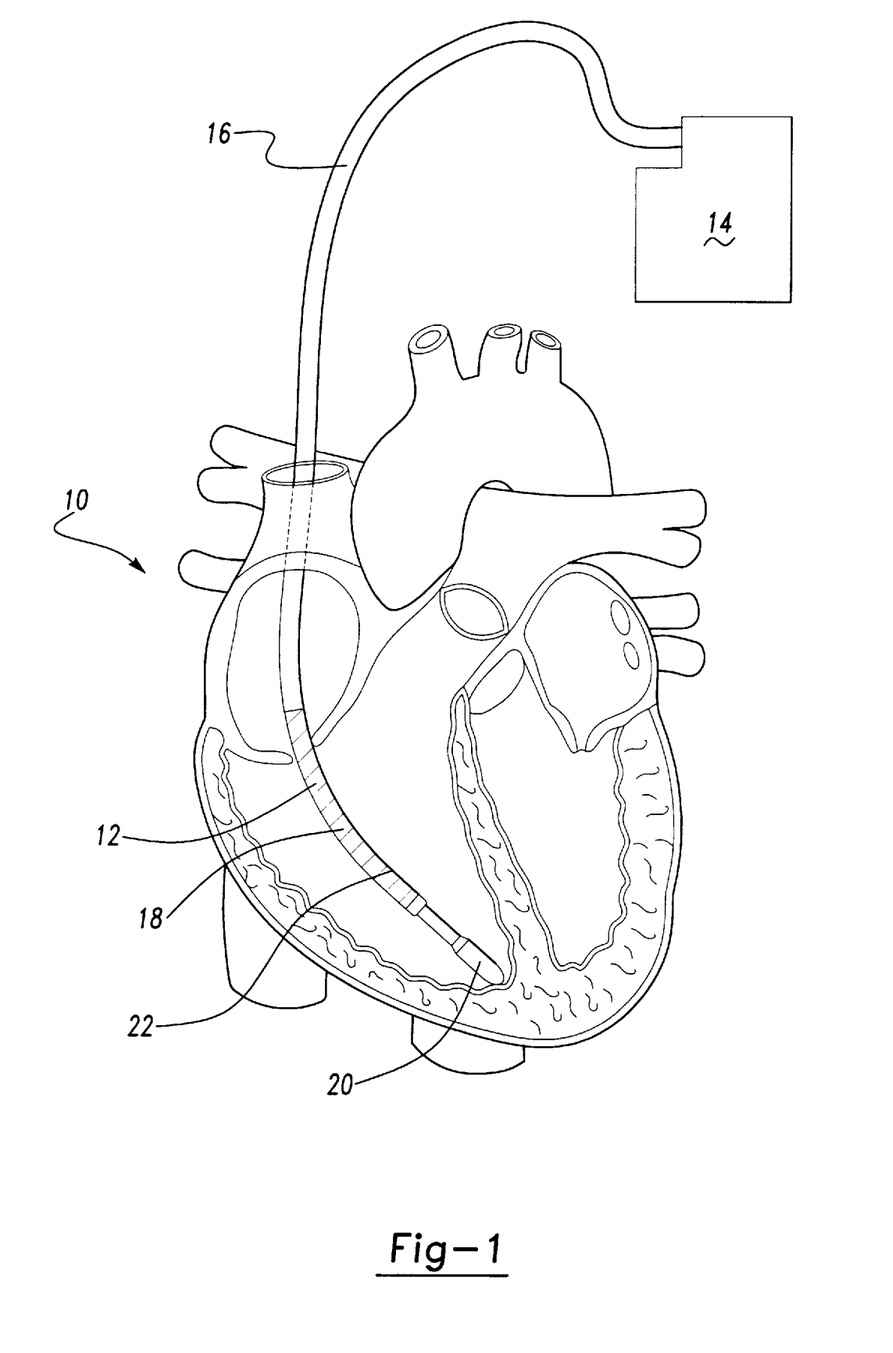
FIG. 1 is a cross-sectional representation of the human heart having an implanted electrode positioned therein.

As discussed, the present invention relates to an implantable cardioverter defibrillator and associated electrodes, as illustrated in FIG. 1. A sectional view of a human heart, generally illustrated as 10, is shown. Positioned substantially within the right ventricle of the heart is an intraventricular catheter 12. The catheter 12 is electronically connected to an implantable cardioverter device or active ICD can 14 by a lead 16. The catheter 12 includes a coiled region 18. The implantable cardioverter device 14 is considered "ground" and is implanted pectorally.

According to the present invention, the catheter 12 has formed thereon a first electrode or sensor region 20 and a second electrode or sensor region 22. The first electrode or sensor region 20 is formed substantially on the tip of the catheter 12, while the second electrode or sensor region 22 is formed on the coiled region 18 of the catheter 12. The regions 20 and 22 are relatively closely spaced.

As noted above, two unipolar signals are derived according to the method and apparatus of the present invention. According to this construction, one unipolar signal is measured between the tip of the catheter 12 to the active ICD can 14. The other unipolar is from the coil 18 of the catheter 12 to the active ICD can 14. This arrangement eliminates the need for multiple leads.

As noted above, the regions 20 and 22 produce electrograms via the active ICD can 14 which demonstrate similar morphology and consistency during rhythms with broad coherent activation (such as sinus rhythm and ventricular tachycardia). Conversely, for incoherent rhythms (ventricular fibrillation and polymorphic ventricular tachycardia), activation between the electrodes proved to be dissimilar and inconsistent. The cross-correlation of the two depolarizations measures similarity between electrogram morphology, and interquartile range measures consistency in a passage.

It should be noted that while the catheter of FIG. 1 has been discussed and illustrated, this is only exemplary and other electrode configurations may well be selected to achieve the intended results of the present invention.

Figure 2:
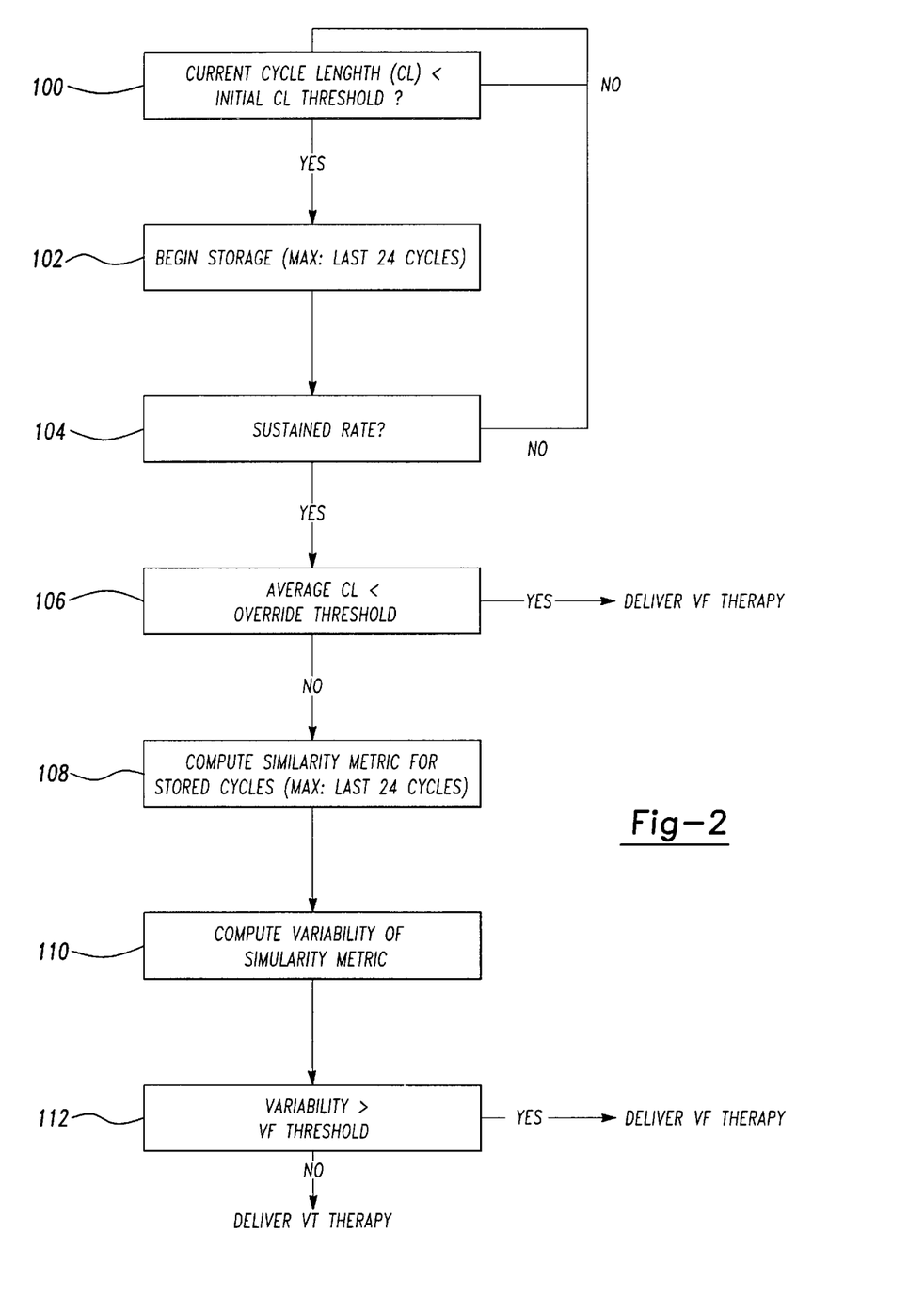
FIG. 2 is a functional flow chart illustrating the steps taken according to the present invention to differentiate between ventricular tachycardia and ventricular fibrillation.

FIG. 2 is a functional flow chart illustrating the steps taken according to the present invention to differentiate between ventricular tachycardia and ventricular fibrillation. Specifically, the flowchart of FIG. 2 defines paired signal concordance algorithm (PSC) integrated with rate detection. The digitized signal is not stored at step 102 until the device determines that there is a high rate (short cycle length) at Step 100. Each cycle from that point is saved, keeping only the last 24 cycles.

Once the rate is considered sustained at Step 104 and that therapy is needed, an override step at Step 106 determines if the rhythm is extremely fast as indicated by relative rates. If so, there is no question that ventricular fibrillation therapy is needed and PSC will not be invoked. If not, the PSC algorithm is invoked to determine which therapy is appropriate. The first step at Step 108 of PSC calculates the similarity between the two unipolar signals for the stored cycles. The second step at Step 110 measures the variability of these measurements.

The variability is the measure which separates ventricular fibrillation and ventricular tachycardia. If the variability is found to be above a given threshold at Step 112, the device should deliver ventricular fibrillation therapy. If the variability is below a given threshold, the device should deliver ventricular tachycardia therapy. Normalized cross-correlation and interquartile range are ways to measure similarity and variability, respectively.

It should be understood that the method desecribed above is exemplary, and modifications of these steps may be made to achieve the various objects of the present invention.

The present invention will be further understood according to the following description of an Example of the invention as practiced on a patient.

EXAMPLE

Figure 3:
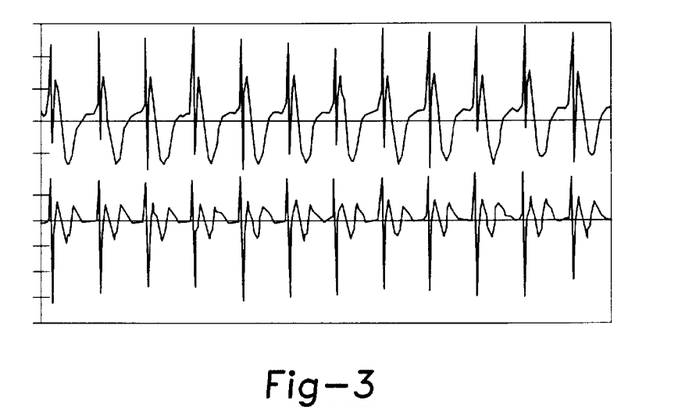
FIG. 3 is an exemplary sample of a sinus rhythm wave form.
Figure 4:
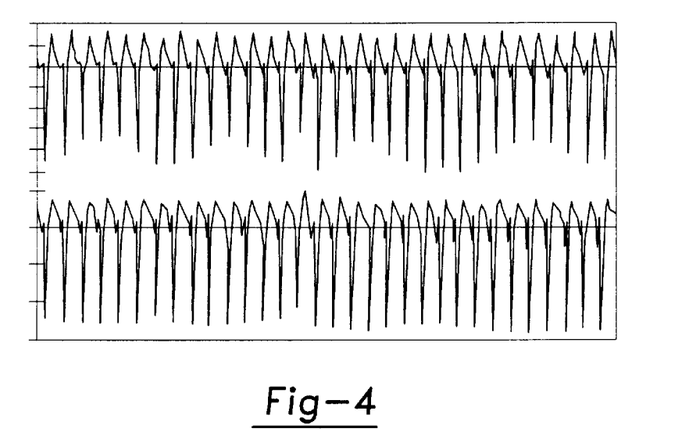
FIG. 4 is an exemplary sample of a ventricular tachycardia waveform.
Figure 5:
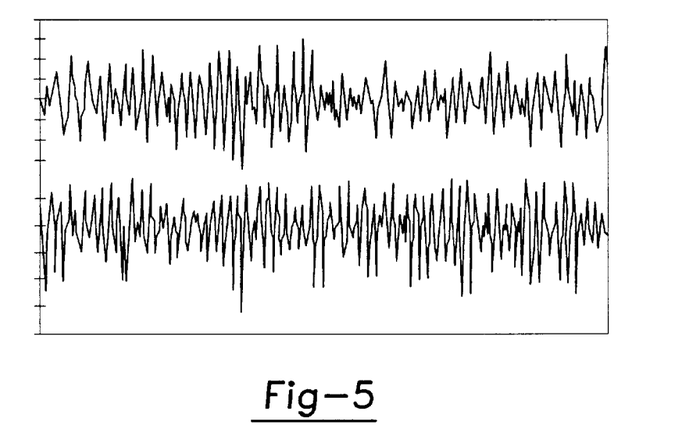
FIG. 5 is an exemplary sample of a ventricular fibrillation waveform.

Two unipolar electrograms were derived from the distal and proximal electrodes of a catheter with 1 cm spacing which was located in the right ventricular apex during electrophysiology studies. A wire located remotely in the femoral vein was used as the reference electrode. This configuration is similar to what is presently used. Sinus rhythm, ventricular tachycardia, and ventricular fibrillation from 10 patients were recorded on FM tape at 3¾ ips, filtered at 1–500 Hz., and digitized at 1000 Hz. A sample of a sinus rhythm wave form is shown in FIG. 3. The top electrogram is distal unipolar and the bottom electrogram is proximal unipolar. An example of a ventricular tachycardia waveform is shown in FIG. 4. An example of a ventricular fibrillation waveform is shown in FIG. 5. A ten second passage is shown in each of FIGS. 3, 4, and 5.

Depolarization locations were determined using a custom auto-adjusting threshold trigger (sensitivity 0.75, time constant 0.5 s). Two of the ten patients were used in the development of this method (training) and the remaining were used for testing.

Figure 6:
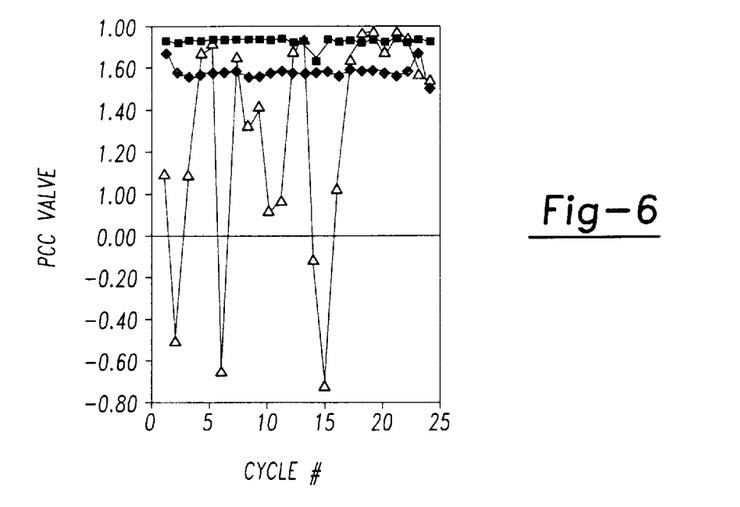
FIG. 6 is a plot of the peak cross correlation for each beat of an exemplary patient.

Sensitivity and specificity values were derived for all patients where: Ho: sinus rhythm, ventricular tachycardia and H1: ventricular fibrillation. In this study, particular attention was paid to separating ventricular fibrillation which would need immediate positive identification. A plot of the PCC for each beat of an exemplary patient is show in FIG. 6. According to this plot, the peak cross-correlation values are illustrated along the y-axis for each cycle as illustrated on the x-axis. (Diamonds denote sinus rhythm, squares denote ventricular tachycardia, and triangles denote ventricular fibrillation.) As illustrated, sinus rhythm and ventricular tachycardia exhibit values near 1 for the entire passage while ventricular fibrillation exhibits a large variance.

Figure 7:
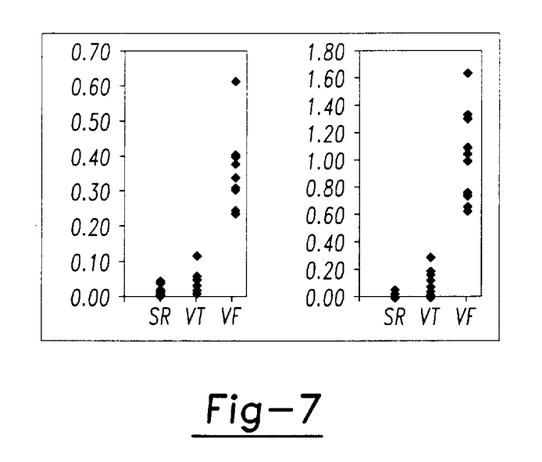
FIG. 7 is a comparison of a standard deviation and an interquartile range plotted for an exemplary patient.

Quantifying the variance was achieved by both standard deviation and interquartile range as illustrated in FIG. 7. According to this illustration, standard deviation is shown on the left and interquartile range on the right. From the graph, patient-independent thresholds chosen between 0.15 and 0.25 for STD and 0.3 and 0.6 would give 100% sensitivity and 100% specificity in separation of ventricular fibrillation from ventricular tachycardia and sinus rhythm.

In order to analyze the performance of this algorithm on coherent, but polymorphic rhythms two passages of sinus rhythm with premature ventricular depolarizations and generated STD and IQR values. Results show STD and IQR fall in the sinus rhythm/ventricular tachycardia range. Therefore, this rhythm would not be misdiagnosed by this method.

Two passages of polymorphic ventricular tachycardia were also tested with the method and were easily diagnosed as incoherent (ventricular fibrillation range). This is acceptable since this rhythm would require defibrillation therapy.

Figure 8:
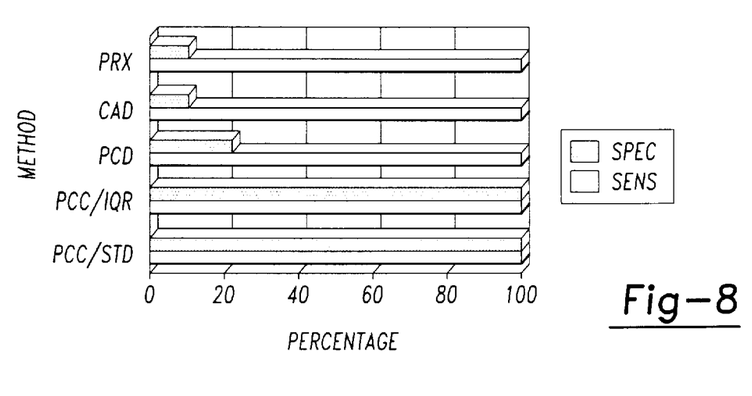
FIG. 8 is an exemplary comparison of implantable cardioverter device detection algorithm results according to the method of the present invention.

The same dataset was also tested on simulations of three commercially available ICDs: Medtronic, Inc. Jewel PCD 7219 (PCD), Ventritex, Inc. Cadence V-100 (CAD), and Cardiac Pacemaker, Inc. Ventak PrX 1700 (PRX), for their nominal settings. Sensitivity for ventricular fibrillation detection was 100 percent, but specificity ranged from only 10 to 20 percent for all devices, i.e., 90 percent of ventricular tachycardias were misdiagnosed as ventricular fibrillation. The invention has been shown to improve specificity to 100 percent. This is illustrated in FIG. 8 which shows a comparison of implantable cardioverter device detection algorithm results with methods according to the present invention, where SENS is sensitivity and SPEC is specificity.

ALTERNATIVE METHODS

Computational complexity remains a feature of this method.

However, the cross-correlation is only one measure of similarity between electrograms. Replication may be possible by modifying simpler template-based algorithms (DOA, BAM, DAM) whereby the second channel would replace the template. IQR is successful in measuring consistency in order to derive an episode diagnosis.

Other measures of variability include STD, X of Y criterion, and range. In addition, adaptive filtering techniques might be an excellent choice for quantifying the variance of the similarity between the two signals. This algorithm could be implemented in hardware or in a DSP chip.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

We claim:

1. A method for differentiating between ventricular tachycardia and ventricular fibrillation, the method including the steps of:

forming a first sensor for placement in sensory association with the heart for producing a first signal;

forming a second sensor for placement in sensory association with the heart for producing a second signal;

forming a signal receiving apparatus for receiving said first and second signals and for producing configurations based upon said first and second signals;

forming a coherence determining apparatus for determining coherence of said signals based on said configuration;

distinguishing between ventricular tachycardia and ventricular fibrillation:

causing said apparatus for receiving said signals to form configurations based on said first and second signal; and causing said apparatus for determining coherence to determine whether or not coherence between said configurations exists.

2. The method for differentiating between ventricular tachycardia and ventricular fibrillation according to claim 1 including the step of forming said first and second sensors on a catheter.

3. The method for differentiating between ventricular tachycardia and ventricular fibrillation according to claim 1, including the step of determining whether or not therapy is required by determining whether or not said first and said second signals received by a signal receiving apparatus should be saved.

4. The method for differentiating between ventricular tachycardia and ventricular fibrillation according to claim 3, including the steps of identifying a sufficiently high rate of signals and saving said at least one digitized signal and all signals thereafter received.

5. The method for differentiating between ventricular tachycardia and ventricular fibrillation according to claim 4, wherein said number of digitized signals defines at least 24 cycles and wherein said method includes the step of keeping only the last 24 cycles of the digitized signals saved.

6. The method for differentiating between ventricular tachycardia and ventricular fibrillation according to claim 1, including the step of invoking a signal concordance algorithm based upon first and second signals.

7. The method for differentiating between ventricular tachycardia and ventricular fibrillation according to claim 6, including the step of calculating the similarity between said signals produced by said first sensor and said second sensor.

8. An apparatus for differentiating between ventricular tachycardia and ventricular fibrillation, said mechanism comprising:

a first sensor for placement in sensory association with the heart for producing a first signal;

a second sensor for placement in sensory association with the heard for producing a second signal;

a signal receiving apparatus for receiving said first and second signals and for producing configurations based upon said first and second signals, said first and second sensors being operatively associated with said signal receiving apparatus;

a coherence determining apparatus for determining coherence of said signals based on said configuration, said coherence determining apparatus being operatively associated with said signal receiving apparatus: and means for differentiating between ventricular tachycardia and ventricular fibrillation, said means being operatively associated with said coherence determining apparatus and being responsive thereto.

9. The apparatus for differentiating between ventricular tachycardia and ventricular fibrillation of claim 8, said apparatus further including an electrode catheter, said first and second sensors being fitted to said electrode catheter in operative association therewith.

10. A method for differentiating between ventricular tachycardia and ventricular fibrillation, the method including the steps of:

determining whether or not at least one digitized signal received by a signal receiving apparatus should be saved;

saving said at least one digitized signal;

determining that the rate of the received signal is sustained based upon said at least one digitized signal; and determining the type of therapy to be administered based upon said at least one saved digitized signal.

11. The method for differentiating between ventricular tachycardia and ventricular fibrillation according to claim 10, wherein the step of saving at least one digitized signal further includes the step of saving said at least one digitized signal after a sufficiently high rate of signals is identified.

12. The method for differentiating between ventricular tachycardia and ventricular fibrillation according to claim 11, wherein said number of digitized signals defines at least 24 cycles and wherein the step of saving at least one digitized signal further includes the step of keeping only the last 24 cycles of said at least one digitized signal saved.

13. The method for differentiating between ventricular tachycardia and ventricular fibrillation according to claim 10, wherein ventricular activity is defined by ventricular rhythm and wherein said method includes the step of delivering ventricular fibrillation therapy when it is determined that said rhythm meets a threshold speed.

14. The method for differentiating between ventricular tachycardia and ventricular fibrillation according to claim 10, wherein said signal receiving apparatus includes at least two separate sensors and wherein said method includes the step of invoking a signal concordance algorithm based upon signals from at least two separate sensors to determine the type of therapy to be delivered.

15. The method for differentiating between ventricular tachycardia and ventricular fibrillation according to claim 14, wherein the step of invoking a signal concordance algorithm further includes the step of storing cycles and the step of calculating the similarity between said signals produced by said at least two separate sensors for said stored cycles.

16. The method for differentiating between ventricular tachycardia and ventricular fibrillation according to claim 15, wherein the step of invoking a signal concordance algorithm further includes the step of storing cycles and the step of measuring the variability of the calculations produced from measuring said similarity.

17. The method for differentiating between ventricular tachycardia and ventricular fibrillation according to claim 16, in which said variability is the measure which separates ventricular fibrillation from ventricular tachycardia.

18. The method for differentiating between ventricular tachycardia and ventricular fibrillation according to claim 17, wherein a threshold is established above which ventricular fibrillation therapy is delivered.

19. The method for differentiating between ventricular tachycardia and ventricular fibrillation according to claim 17, wherein a threshold is established below which ventricular tachycardia therapy is delivered.

20. The method for differentiating between ventricular tachycardia and ventricular fibrillation according to claim 15, wherein said at least two separate sensors are provided on a single catheter.

* * * * *

UNITED STATES PATENT AND TRADEMARK OFFICE
CERTIFICATE OF CORRECTION

PATENT NO. : 5,857,977
DATED : January 12, 1999
INVENTOR(S) : Stephanie A. Caswell, et al.

It is certified that error appears in the above-indentified patent and that said Letters Patent is hereby corrected as shown below:

Column 4, line 10

"of" should be --in--.

Column 4, line 18

"ICDS," should be --ICDs,--.

Column 4, line 62

"241-149)," should be --241-249),--.

Column 8, line 63 after "unipolar" insert --signal--.

Column 9, line 17

"flowchart" should be --flow chart--.

Column 10, line 28 after "values" insert --were tested--.

Column 11, line 23, Claim 1

"fibrillation:" should be --fibrillation;--

UNITED STATES PATENT AND TRADEMARK OFFICE
CERTIFICATE OF CORRECTION

PATENT NO. : 5,857,977
DATED : January 12, 1999
INVENTOR(S) : Stephanie A. Caswell, et al.

It is certified that error appears in the above-indentified patent and that said Letters Patent is hereby corrected as shown below:

Column 11, line 65, Claim 8

"heard" should be --heart--.

Column 12, line 7, Claim 8

"apparatus:" should be --apparatus;--

Signed and Sealed this

Twelfth Day of October, 1999

*Attest:*

Q. TODD DICKINSON

*Attesting Officer*   Acting Commissioner of Patents and Trademarks